United States Patent
Yamamoto et al.

(10) Patent No.: US 10,758,123 B2
(45) Date of Patent: Sep. 1, 2020

(54) OPHTHALMOLOGICAL MICROSCOPE SYSTEM

(71) Applicant: KABUSHIKI KAISHA TOPCON, Itabashi-ku, Tokyo (JP)

(72) Inventors: Satoshi Yamamoto, Saitama (JP); Ikuo Ishinabe, Saitama (JP); Michiko Nakanishi, Tokyo (JP)

(73) Assignee: KABUSHIKI KAISHA TOPCON, Itabashi-ku, Tokyo (JP)

( * ) Notice: Subject to any disclaimer, the term of this patent is extended or adjusted under 35 U.S.C. 154(b) by 432 days.

(21) Appl. No.: 15/738,807

(22) PCT Filed: Feb. 3, 2016

(86) PCT No.: PCT/JP2016/053285
§ 371 (c)(1),
(2) Date: Dec. 21, 2017

(87) PCT Pub. No.: WO2017/002381
PCT Pub. Date: Jan. 5, 2017

(65) Prior Publication Data
US 2018/0184897 A1    Jul. 5, 2018

(30) Foreign Application Priority Data

Jun. 30, 2015   (JP) ................. 2015-132087

(51) Int. Cl.
*A61B 3/13*     (2006.01)
*A61F 9/007*    (2006.01)
(Continued)

(52) U.S. Cl.
CPC ............ *A61B 3/13* (2013.01); *A61B 3/102* (2013.01); *A61B 3/135* (2013.01); *A61B 3/18* (2013.01); *A61F 9/007* (2013.01); *A61F 9/008* (2013.01)

(58) Field of Classification Search
CPC .......... A61B 3/14; A61B 3/0025; A61B 3/12; A61B 3/102; A61B 3/0058; A61B 3/1225;
(Continued)

(56) References Cited

U.S. PATENT DOCUMENTS 8,049,873 B2    11/2011 Hauger et al.
2010/0157311 A1*   6/2010 Hayashi ............... A61B 3/1025
356/496

(Continued)

FOREIGN PATENT DOCUMENTS

JP    2015-104582 A    6/2015

OTHER PUBLICATIONS

International Search Report and Written Opinion dated May 10, 2016, in connection with International Patent Application No. PCT/JP2016/053285, 5 pgs.

*Primary Examiner* — Thomas K Pham
*Assistant Examiner* — Sharrief I Broome
(74) *Attorney, Agent, or Firm* — Chiesa Shahinian & Giantomasi PC

(57) ABSTRACT

An ophthalmological microscope system, having an illumination system that projects illumination light onto a subject's eye. A light receiving system guides returning light of the illumination light to an image sensor or an eyepiece system. An interference optical system splits light into measurement light and reference light and detects interference light generated from returning light of the measurement light and the reference light. A designation unit is used for designating an operation mode. When an observation priority mode (or an OCT priority mode) has been designated, a controller executes first light amount control that restricts light amount of the measurement light (or second light amount control that restricts light amount of the illumination
(Continued)

light) to make total light amount of the illumination light and the measurement light equal to or less than a predetermined value.

16 Claims, 7 Drawing Sheets

(51) Int. Cl.
*A61B 3/135* (2006.01)
*A61F 9/008* (2006.01)
*A61B 3/10* (2006.01)
*A61B 3/18* (2006.01)

(58) Field of Classification Search
CPC ..... A61B 3/0008; A61B 3/113; A61B 3/1025; A61B 3/145; A61B 3/0041; A61B 3/0091; A61B 3/103; A61B 3/1005; A61B 3/1015; A61B 3/117; A61B 3/112; A61B 3/107; A61B 3/13; A61B 3/0033; G01B 9/02091; G01B 9/02044; G01B 9/02004; G01B 9/02027; G01B 2290/45; G01B 2290/70; G01B 9/0203; G01B 9/02083; G01B 2290/65; G01B 9/02041; G01B 9/02087; G01B 11/2518; G01B 9/0201; G01B 9/02011; G01B 9/02028; G01B 9/02034; G01B 9/02039; G01B 9/02045; G01B 9/02048; G01B 9/0205; G06T 2207/30041; G06T 2207/10101; G06T 7/0012; G06T 2207/20056; G06T 2207/30104; G06T 5/50; G06T 7/0016; G06T 7/248; G06T 7/337; G06T 15/00; G06T 15/04; G06T 2207/10028; G06T 2207/10048; G06T 2207/10144; G06T 2207/20081; G06T 2207/30096; G06T 2207/30101; G06T 3/0018; G06T 3/0062; G06T 3/4053; G02B 27/141; G02B 26/101; G02B 27/0068; G02B 2027/0187; G02B 26/0833; G02B 27/1013; G02B 7/023; G02B 7/04; G02B 13/0095; G02B 17/006; G02B 17/08; G02B 17/0832; G02B 2027/0118; G02B 2027/0127; G02B 2027/0138; G02B 2027/014; G02B 2027/0178; G02B 2027/0185; G02B 21/0012; G02B 21/0048
See application file for complete search history.

(56) References Cited

U.S. PATENT DOCUMENTS

| | | | |
|---|---|---|---|
| 2012/0092615 A1* | 4/2012 | Izatt | G01B 9/02091 351/206 |
| 2014/0111768 A1* | 4/2014 | Komine | A61B 3/14 351/206 |
| 2015/0182111 A1* | 7/2015 | Namiki | A61B 3/0025 351/206 |
| 2017/0209044 A1* | 7/2017 | Ito | A61B 3/0091 |

* cited by examiner

OPHTHALMOLOGICAL MICROSCOPE SYSTEM

CROSS-REFERENCE TO RELATED APPLICATIONS

This application is a national stage (under 35 U.S.C. 371) of International Patent Application No. PCT/JP2016/053285, filed Feb. 3, 2016, which claims priority to Japanese Patent Application No. 2015-132087, filed Jun. 30, 2015, both of which are herein incorporated by reference in their entirety.

TECHNICAL FIELD

Embodiments described herein relate generally to an ophthalmological microscope system.

BACKGROUND

Various kinds of microscopes are utilized for magnified observation of an eye in the field of ophthalmology. Examples of such ophthalmological microscopes include slit lamp microscopes and surgical microscopes. There are ophthalmological microscopes that include an image sensor for imaging an eye, and those that include a binocular optical system that provides binocular disparity for stereoscopic observation.

The ophthalmological microscopes may be used in combination with another ophthalmological apparatus. For example, as disclosed in U.S. Pat. No. 8,049,873 (Patent Document 1), a system is known in which an optical coherence tomography (OCT, hereinafter) apparatus is combined with an ophthalmological microscope. The OCT apparatus is utilized for, for example, acquiring cross sectional images, acquiring three dimensional images of an eye, measuring the sizes of ocular tissues (e.g., the thickness of the retina), and acquiring functional information on an eye (e.g., the blood flow information).

[Patent Document 1] U.S. Pat. No. 8,049,873

To ophthalmic instruments that project light toward or into eyes, a standard that prescribes requirements concerning the safety of light radiation is applied. Such standards include standards concerning protection of eyes from light hazards and the like. Protection of the eye from light hazards is prescribed in, for example, International Organization for Standardization (ISO) 15004-2: 2007 (Ophthalmic instruments—Fundamental requirements and test methods—Part 2: light hazard protection) (JIST 15004-2: 2013).

However, in the system in which an OCT apparatus is combined with an ophthalmological microscope, for example, there are cases in which illumination light from the ophthalmological microscope and measurement light from the OCT apparatus are simultaneously projected onto the subject's eye in order to acquire OCT images during surgery. In the case of projecting both the illumination light and the measurement light onto the subject's eye while satisfying the aforementioned standards, there are cases in which the amount of the illumination light or the amount of the measurement light to be projected onto the subject's eye becomes insufficient. If the amount of the illumination light or the amount of the measurement light are insufficient, the image quality of an observation image based on the returning light of the illumination light or the image quality of an OCT image deteriorates. To deal with this problem, if the amount of the illumination light or the amount of the measurement light is increased, the aforementioned standards cannot be satisfied and there is a danger of harmful influence on the subject. As described thus far, there is a trade-off relationship between the safety of the subject's eye and the improvement of the image quality. This brings upon a problem of difficulty in satisfying both the safety of the subject's eye and the improvement of the image quality.

BRIEF SUMMARY OF THE EMBODIMENTS

The present invention has been developed for solving the aforementioned problem and an object thereof is to provide a new technique capable of improving the image quality of the observation image and the image quality of the OCT image while securing the protection of the subject's eye from light hazards in the case where the OCT apparatus is combined with the ophthalmological microscope.

An ophthalmological microscope system of an embodiment includes an illumination system, a light receiving system, an interference optical system, a designation unit, and a controller. The illumination system projects illumination light onto a subject's eye. The light receiving system guides returning light of the illumination light that has been projected onto the subject's eye to an image sensor or an eyepiece system. The interference optical system splits light from an OCT light source into measurement light and reference light and detects interference light generated from returning light of the measurement light projected onto the subject's eye and the reference light. The designation unit is used for designating an operation mode. The controller executes first light amount control that restricts light amount of the measurement light to make total light amount of the illumination light and the measurement light equal to or less than a predetermined value when an observation priority mode has been designated using the designation unit. The controller executes second light amount control that restricts light amount of the illumination light to the total light amount equal to or less than the predetermined value when an OCT priority mode has been designated using the designation unit.

According to the embodiment, the image quality of the observation image and the image quality of the OCT image can be improved while securing the protection of the subject's eye from light hazards in the case where the OCT apparatus is combined with the ophthalmological microscope.

DESCRIPTION OF THE EMBODIMENTS

Exemplary embodiments of an ophthalmological microscope system according to the present invention will be described in detail with reference to the drawings. The contents of the documents cited in the present specification and any known techniques can be incorporated into the following embodiments.

An ophthalmological microscope system is used for observing (and photographing) a magnified image of the subject's eye for a diagnosis, treatment and/or surgery in the field of ophthalmology. The site to be observed may be an arbitrary site of the patient's eye. For example, the site to be observed may be any site in the anterior segment such as the cornea, the corner angle, the vitreous body, the crystalline lens, or the ciliary body, and/or may be any site in the posterior segment such as the retina, the choroid, or the vitreous body. The site to be observed may also be any peripheral site of the eye such as the eyelid or the eye socket.

In addition to the function as a microscope used for magnified observation of the subject's eye, the ophthalmological microscope system includes a function as another ophthalmological apparatus. In the following embodiment, the ophthalmological microscope system has an OCT function as a function as another ophthalmological apparatus. In addition to the OCT function, the function as another ophthalmological apparatus may include laser treatment, ocular axial length measurement, refractive power measurement, higher order aberration measurement, or the like. Alternatively, the ophthalmological microscope system may have the function of laser treatment, ocular axial length measurement, refractive power measurement, higher order aberration measurement, or the like instead of the OCT function. Another ophthalmological apparatus may have an arbitrary configuration capable of performing examination, measurement, or imaging of the subject's eye by means of an optical system method.

Hereinafter, described is a case in which the embodiment is applied to an ophthalmological microscope system that provides an image of the subject's eye to the observer by guiding the returning light of the illumination light that has been projected onto the subject's eye to the image sensor and by displaying an image based on the output from the image sensor on the display unit provided in the eyepiece unit. However, it is also possible to apply the embodiment described below to an ophthalmological microscope system that provides an image of the subject's eye to the observer by guiding the returning light of the illumination light that has been projected onto the subject's eye to the eyepiece system.

Figure 1:
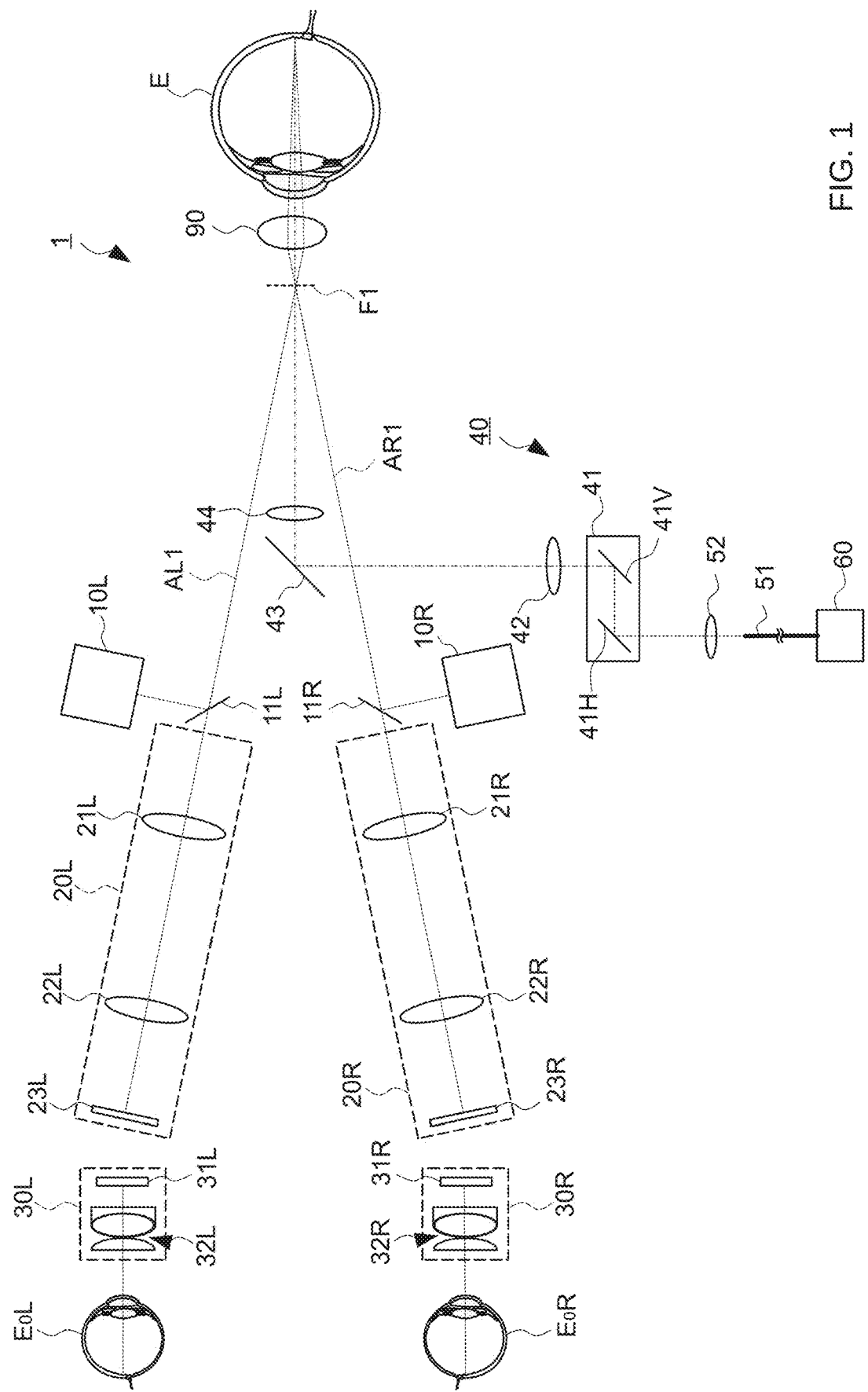
FIG. 1 is a schematic diagram illustrating an example of the configuration of the ophthalmological microscope system according to the embodiment.
Figure 2:
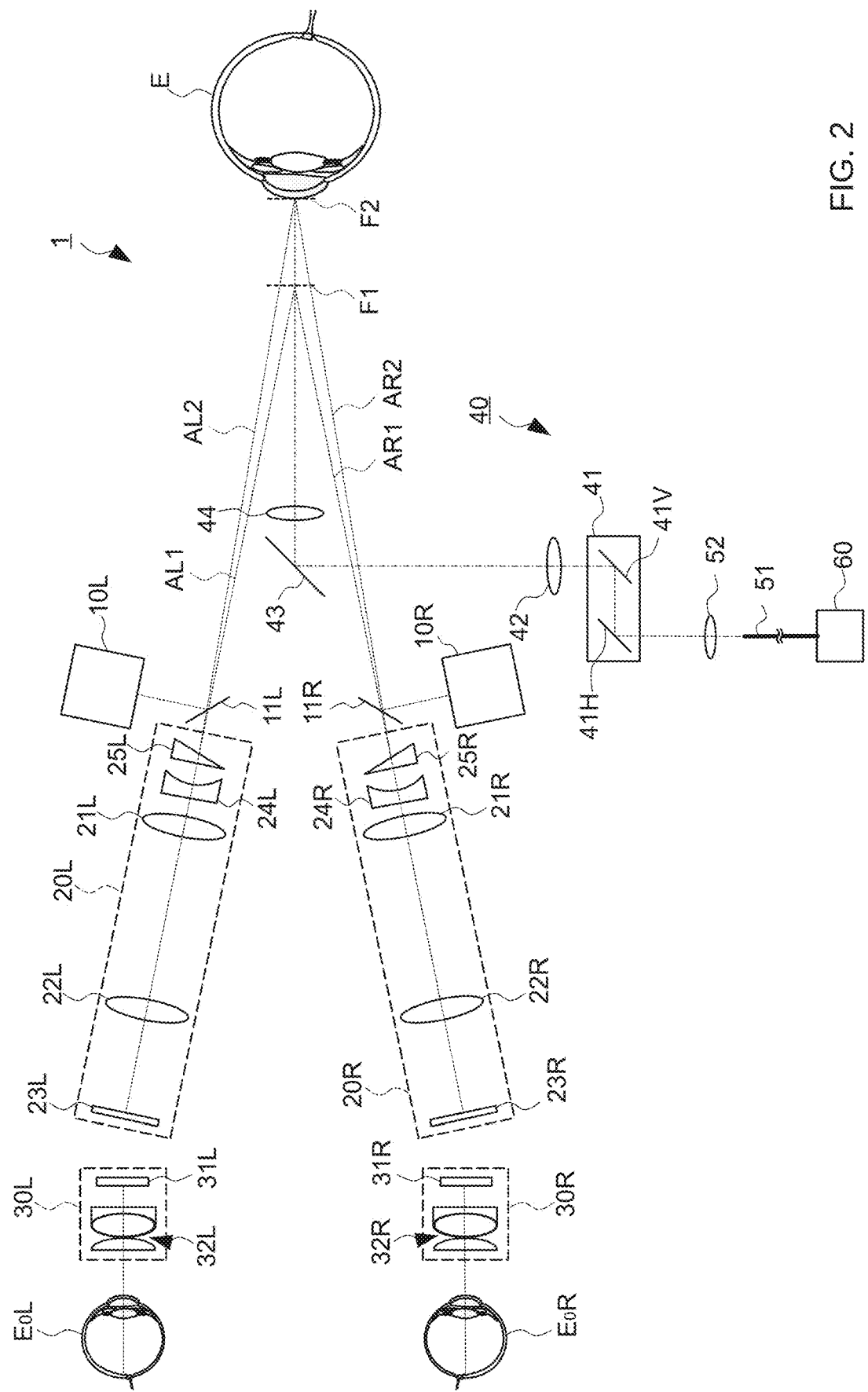
FIG. 2 is a schematic diagram illustrating an example of the configuration of the ophthalmological microscope system according to the embodiment.
Figure 3:
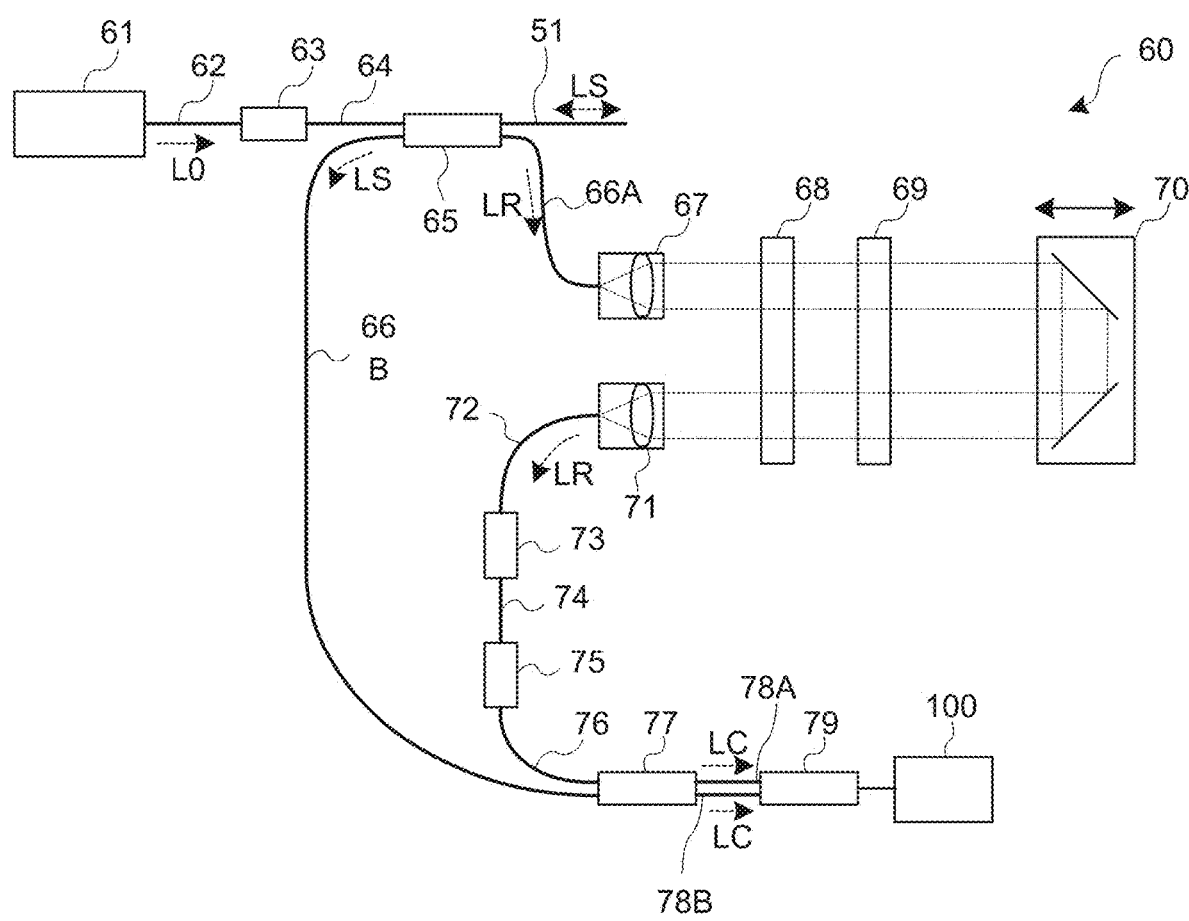
FIG. 3 is a schematic diagram illustrating an example of the configuration of the ophthalmological microscope system according to the embodiment.
Figure 4:
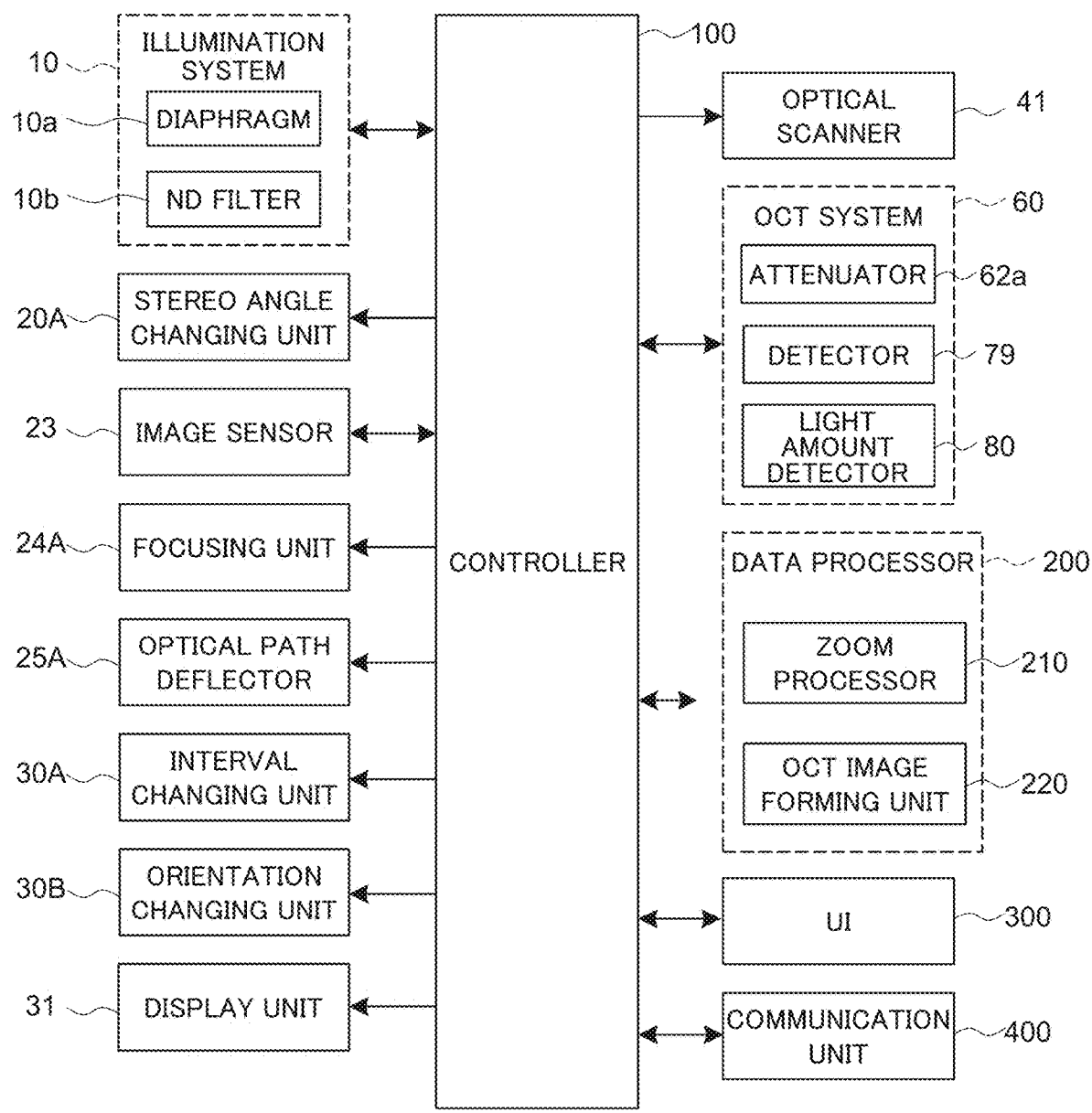
FIG. 4 is a schematic diagram illustrating an example of the configuration of the ophthalmological microscope system according to the embodiment.

FIG. 1 to FIG. 5 illustrate an exemplary configuration of the ophthalmological microscope system according to the embodiment. FIG. 1 to FIG. 3, and FIG. 5 illustrate an exemplary configuration of the optical system of the ophthalmological microscope system. FIG. 1 illustrates the optical system used when observing the posterior segment, and FIG. 2 illustrates the optical system used when observing the anterior segment. FIG. 4 illustrates the configuration of the processing system.

The ophthalmological microscope system 1 includes the illumination system 10 (10L and 10R), the light receiving system 20 (20L and 20R), the eyepiece system 30 (30L and 30R), the projection system 40, and the OCT system 60.

When observing the posterior segment (the retina, etc.), the front lens 90 is disposed right in front of the subject's eye E. It is possible to use a contact lens or the like instead of the front lens 90 of a non-contact type as shown in FIG. 1. When observing the corner angle, it is possible to use a contact mirror (a triple mirror, etc.) or the like.

The illumination system 10 projects illumination light onto the subject's eye E. Although not shown, the illumination system 10 includes a light source that emits illumination light, a diaphragm that defines an illumination field according to a variable aperture value, a lens system, and the like. The illumination system 10 is capable of changing at least one of the light amount and the intensity of the illumination light projected onto the subject's eye E under the control of the controller 100 described later. The "intensity" of light is the light amount per unit time in a unit area, and the "light amount" is a physical quantity obtained by time integration of the "intensity". Therefore, in the following embodiment, the "light amount" and the "intensity" may not be distinguished from each other unless otherwise mentioned.

For example, a light source, which emits illumination light, emits illumination light with light amount corresponding to a control amount (voltage value, electric current value, etc.) designated by a control signal from the controller 100. With this, the controller 100 is capable of changing the light amount of the illumination light by controlling the light source. In addition, the controller 100 can acquire the control amount (voltage value, electric current value, etc.) set for the light source, and can detect the light amount of the illumination light corresponding to the acquired control amount. For example, the controller 100 stores, in advance, a control table in which control amounts are associated with corresponding light amounts of the illumination light. By referring to the control table, the controller 100 determines the light amount of the illumination light corresponding to the control amount acquired. Alternatively, the illumination system 10 may include an illumination light amount detector that detects the light amount of illumination light emitted from the light source. In this case, the controller 100 can detect the light amount of the illumination light based on a detection result obtained by the illumination light amount detector.

Further, it is possible to change the light amount of the illumination light to be projected onto the subject's eye E by designating the aperture value in response to a control signal from the controller 100. The illumination system 10 may be configured to be capable of changing the projection angle of the illumination light with respect to the subject's eye E by changing the orientation of the light source or by changing the angle of the beam splitter 11L (11R) described later with respect to the optical axis of the light receiving system 20. It is possible to change the light amount of the illumination light to be projected onto the subject's eye E by changing the projection angle of the illumination light based on a control signal from the controller 100.

The illumination system 10 may include an ND (Neutral Density) filter that reduces the light amount of the illumination light. The ND filter is a light attenuating filter that can be inserted into and removed from the optical path of the illumination light. In this case, the illumination system 10 includes a movement mechanism (not shown) for inserting the ND filter into the optical path of the illumination light and removing the ND filter from the optical path of the illumination light. The movement mechanism receives a control signal from the controller 100, and inserts the ND filter into the optical path of the illumination light or removes the ND filter from the optical path of the illumination light based on the control signal received. With this, it is possible to change the light amount of the illumination light to be projected onto the subject's eye E. The ND filter may be inserted into and removed from an arbitrary position in the illumination optical path.

The configuration of the illumination system 10 may be similar to that in any conventional ophthalmologic apparatus (e.g., a slit lamp microscope, a fundus camera, a refractometer, etc.).

The illumination systems 10L and 10R of the present embodiment are configured coaxially with the light receiving systems 20L and 20R, respectively. More specifically, the beam splitter 11L, which may be a half mirror, is obliquely provided in the left light receiving system 20L for acquiring an image to be presented to the left eye $E_oL$ of the observer. The beam splitter 11L coaxially couples the optical path of the left illumination system 10L to the optical path of the left light receiving system 20L. The illumination light outputted from the left illumination system 10L is reflected by the beam splitter 11L and illuminates the subject's eye E coaxially with the left light receiving system 20L. Similarly, the beam splitter 11R, which couples the optical path of the right illumination system 10R to the optical path of the right light receiving system 20R, is obliquely provided in the right light receiving system 20R for acquiring an image to be presented to the right eye $E_oR$ of the observer. The beam splitter 11R couples the optical path of the right illumination system 10R to the optical path of the right light receiving system 20R in a coaxial manner. The illumination light outputted from the right illumination system 10R is reflected by the beam splitter 11R and illuminates the subject's eye E coaxially with the right light receiving system 20R.

It is possible to have a configuration so that the position of the illumination light with respect to the optical axis of the light receiving system 20L (20R) is variable. This configuration is realized, for example, by providing a means for changing the projection position of the illumination light onto the beam splitter 11L (11R) like conventional microscopes for ophthalmic surgery.

In the present example, the beam splitter 11L (11R) is disposed between the objective lens 21L (21R) and the subject's eye E. However, the position where the optical path of the illumination light is coupled to the light receiving system 20L (20R) may be an arbitrary position in the light receiving system 20L (20R).

The present embodiment includes a pair of left and right light receiving systems 20L and 20R. The left light receiving system 20L has a configuration for acquiring an image to be presented to the left eye $E_oL$ of the observer and the right light receiving system 20R has a configuration for acquiring an image to be presented on the right eye $E_oR$. The left light receiving system 20L and the right light receiving system 20R have the same configuration. The left light receiving system 20L (the right light receiving system 20R) includes the objective lens 21L (21R), the imaging lens 22L (22R), and the image sensor 23L (23R).

It is also possible to employ a configuration in which the imaging lens 22L (22R) is not provided. In the case where the imaging lens 22L (22R) is provided as in the present embodiment, it is possible to form an afocal optical path (a parallel optical path) between the objective lens 21L (21R) and the imaging lens 22L (22R). This makes it easy to dispose an optical element such as a filter and to dispose an optical path coupling member to couple an optical path from another optical system (in other words, the degree of flexibility and expandability of the optical configuration are improved).

The reference symbol AL1 indicates the optical axis (the objective optical axis) of the objective lens 21L of the left light receiving system 20L, and the reference symbol AR1 indicates the optical axis (the objective optical axis) of the objective lens 21R of the right light receiving system 20R. The image sensor 23L (23R) is, for example, an area sensor such as a CCD image sensor or a CMOS image sensor.

The above is the configuration of the light receiving system 20 when observing the posterior segment (the fundus) of the subject's eye E (see FIG. 1). On the other hand, when observing the anterior segment, as shown in FIG. 2, the focus lens 24L (24R) and the wedge prism 25L (25R) are disposed at positions on the subject's eye E side with respect to the objective lens 21L (21R). The focus lens 24L (24R) of the present example is a concave lens and acts to extend the focal length of the objective lens 21L (21R). The wedge prism 25L (25R) changes the direction of the optical path (the objective optical axis AL1 (AR1)) of the left light receiving system 20L (the right light receiving system 20R) outward by a predetermined angle (the deflected optical axes are indicated by the reference symbols AL2 and AR2). In this manner, the focus lens 24L and the wedge prism 25L are disposed in the left light receiving system 20L, and the focus lens 24R and the wedge prism 25R are disposed in the right light receiving system 20R. As a result, the focal position F1 for posterior segment observation is switched to the focal position F2 for anterior segment observation.

A convex lens can be used as the focus lens. In that case, the focus lens is disposed in the optical path at the time of posterior segment observation, and is removed from the optical path at the time of anterior segment observation. Instead of switching the focal length by inserting and removing the focus lens, it is possible to employ a configuration capable of changing the focal length in a continuous or stepwise manner, for example, by providing a focus lens that is movable in the direction along the optical axis.

In the example shown in FIG. 2, the base direction of the wedge prism 25L (25R) is outward (that is, the wedge prism 25L (25R) is disposed in a base-out manner); however, it is possible to apply a wedge prism disposed in a base-in manner. In that case, the wedge prism is disposed in the optical path at the time of observing the posterior segment, and is removed from the optical path at the time of observing the anterior segment. Instead of switching the direction of the optical path by inserting and removing the wedge prism, the provision of a prism, whose prism amount (and prism direction) is variable, gives a configuration that is capable of changing the direction of the optical path in a continuous or stepwise manner.

The present embodiment includes a pair of left and right eyepiece systems 30L and 30R. The left eyepiece system 30L has a configuration for presenting the image of the subject's eye E acquired by the left light receiving system 20L to the left eye $E_oL$ of the observer, and the right eyepiece system 30R has a configuration for presenting the image of the subject's eye E acquired by the right light receiving system 20R to the right eye $E_oR$. The left eyepiece system 30L and the right eyepiece system 30R have the same configuration. The left eyepiece system 30L (the right eyepiece system 30R) includes the display unit 31L (31R) and the eyepiece system 32L (32R).

The display unit 31L (31R) is, for example, a flat panel display such as an LCD. The size of the display surface of the display unit 31L (31R) is, for example, diagonal length of 7 inches or less. The screen sizes of the display devices provided in the pair of the left and right eyepiece systems 30L and 30R are determined under constraints such as the observer's eye width (e.g., the pupillary distance, etc.), the size of the apparatus, the design of the apparatus (e.g., the disposition of the optical systems and mechanisms, etc.) and the like. That is, there is a trade-off relationship between such constraint conditions and the size of the apparent field of view. From such a viewpoint, the maximum screen size of the display units 31L and 31R is considered to be about 7 inches. By devising the configurations of the eyepiece systems 32L and 32R and the disposition of the mechanisms, the display units 31L and 31R that have a screen size exceeding 7 inches can be employed, or the display units 31L and 31R of a small size can be employed.

The interval between the left eyepiece system 30L and the right eyepiece system 30R can be changed. With this, it is possible to adjust the interval between the left eyepiece system 30L and the right eyepiece system 30R according to the eye width of the observer. Further, it is possible to change the relative orientation of the left eyepiece system 30L and the right eyepiece system 30R. That is, the angle formed between the optical axis of the left eyepiece system 30L and the optical axis of the right eyepiece system 30R can be changed. As a result, it becomes possible to induce the convergence of the both eyes $E_0L$ and $E_0R$, thereby being capable of supporting a stereoscopic view by the observer.

The projection system 40 projects light for realizing the function as the aforementioned "another ophthalmological apparatus" onto the subject's eye E from a direction different from those of the objective optical axes (AL1 and AR1, or, AL2 and AR2) of the light receiving systems 20. The projection system 40 of the present example projects light for OCT (referred to as measurement light) onto the subject's eye E.

The projection system 40 includes the optical scanner 41, the imaging lens 42, the deflection mirror 43, and the OCT objective lens 44. Light from the OCT system 60 is guided to the optical scanner 41. The imaging lens 42 may be movable along the optical path of the light from the OCT system 60, thereby functioning as a focus lens. In this case, a movement mechanism (not shown) receives a control signal from the controller 100 (to be described later), and moves the imaging lens 42 by a movement amount in the movement direction, wherein the movement amount and the movement direction are both designated by the control signal.

The light from the OCT system 60 (measurement light) is guided through the optical fiber 51 and exits from the end face of the optical fiber 51. The collimator lens 52 is disposed at a position facing the end face of the optical fiber 51. The collimator lens 52 converts the measurement light emitted from the end face of the optical fiber 51 into a parallel light beam. The measurement light, which has been made into a parallel light beam by the collimator lens 52, is led to the optical scanner 41. Note that the collimator lens 52 may be movable along the optical path of the measurement light so that it can be used as a focus lens (or as one of the lenses constituting a focus lens). In this case, a movement mechanism (not shown) receives a control signal from the controller 100 (to be described later), and moves the collimator lens 52 by a movement amount in the movement direction, wherein the movement amount and the movement direction are both designated by the control signal. Both the imaging lens 42 and the collimator lens 52 may be moved by the movement mechanism in conjunction with each other or independently of one another.

The optical scanner 41 is a two dimensional optical scanner and includes the x scanner 41H that deflects light in the horizontal direction (x direction) and the y scanner 41V that deflects light in the vertical direction (y direction). Each of the x scanner 41H and the y scanner 41V may be an optical scanner of an arbitrary type, and, for example, a galvano mirror can be employed for it. The optical scanner 41 is disposed, for example, at the exit pupil position of the collimator lens 52 or in the vicinity of the exit pupil position. In addition, the optical scanner 41 is disposed, for example, at the entrance pupil position of the imaging lens 42 or in the vicinity of the entrance pupil position.

In the case where a two dimensional optical scanner is configured by combining two one dimensional optical scanners as in the present example, the two one dimensional optical scanners are disposed apart from each other by a predetermined distance (for example, about 10 mm). With this, for example, any one dimensional optical scanner can be disposed at the aforementioned exit pupil position and/or at the aforementioned entrance pupil position.

The imaging lens 42 once converges a parallel light beam (measurement light) that has passed through the optical scanner 41. The light having passed through the imaging lens 42 is reflected by the deflection mirror 43 in the direction of the OCT objective lens 44. The light having passed through the OCT objective lens 44 is projected onto the subject's eye E.

The position of the deflection mirror 43 is determined in advance so that the light guided by the projection system 40 is projected onto the subject's eye E from a direction different from those of the objective optical axes (AL1 and AR1, or, AL2 and AR2) of the light receiving systems 20. In the present example, the deflection mirror 43 is disposed at a position between the left light receiving system 20L and the right light receiving system 20R whose objective optical axes are disposed nonparallelly to each other.

The OCT system 60 includes an interference optical system for performing OCT. FIG. 3 shows an example of the configuration of the OCT system 60. The optical system shown in FIG. 3 is an example of the swept source OCT. The optical system splits light from a wavelength scanning type (wavelength tunable type) light source into measurement light and reference light, generates interference light by superposing the returning light of the measurement light from the subject's eye E and the reference light that has traveled through the reference optical path, and detects the interference light generated. The detection result (detection signal) of the interference light obtained by the interference optical system is a signal indicating a spectrum of the interference light, and is sent to the controller 100.

Like the general swept source OCT apparatus, the light source unit 61 includes a wavelength scanning type (wavelength tunable type) light source capable of scanning (sweeping) the wavelength of emitted light. The light source unit 61 temporally changes the output wavelength in the near infrared wavelength band that cannot be visually recognized by human eyes.

The OCT system 60 can change the light amount of the light L0 output from the light source unit 61 or that of the measurement light LS described later. For example, the light source unit 61 outputs the light L0 with a light amount corresponding to a control amount (voltage value, electric current value, etc.) designated by a control signal input from the controller 100. With this, the controller 100 can change the light amount of the light L0 by controlling the light source unit 61. An attenuator may be provided between the light source unit 61 and the polarization controller 63 (to be described later) and the light amount of the light L0 output from the light source unit 61 may be changed under the control of the controller 100.

An attenuator may be provided in the optical path of the measurement light LS guided to the subject's eye E and the light amount of the measurement light LS may be changed under the control of the controller 100. In this case, another attenuator may also be provided in the optical path of the reference light LR, and the light amount of the reference light LR may be changed according to an amount of change in the light amount of the measurement light LS under the control of the controller 100. In the configuration shown in FIG. 3, the returning light of the measurement light LS returns along the same path as the forward path as described later. Therefore, the light amount of the returning light of the measurement light LS is also changed by the attenuator provided. Thus, when the change amount (attenuation amount) of the light amount of the reference light LR is RA and the change amount (attenuation amount) of the light amount of the measurement light LS is SA, the light amount of the reference light LR may be changed so that RA is larger than SA (RA>SA).

The light L0 output from the light source unit 61 is guided to the polarization controller 63 by the optical fiber 62, and the polarization state of the light L0 is adjusted. In the case where the attenuator is provided between the light source unit 61 and the polarization controller 63, the light L0 is guided to the attenuator by the optical fiber and the light amount of the light L0 is adjusted. The light L0 whose light amount has been adjusted is guided to the polarization controller 63 by the optical fiber 62. The light L0 whose polarization state has been adjusted by the polarization controller 63 is guided to the fiber coupler 65 through the optical fiber 64. The fiber coupler 65 splits the light L0 into the measurement light LS and the reference light LR.

The reference light LR is guided to the collimator 67 by the optical fiber 66A. The reference light LR is converted into a parallel light beam by the collimator 67. Then, the reference light LR is guided to the corner cube 70 via the optical path length correction member 68 and the dispersion compensation member 69. The optical path length correction member 68 acts as a delay element for matching the optical path length (optical distance) of the reference light LR and that of the measurement light LS. The dispersion compensation member 69 acts as a dispersion compensation element for matching the dispersion characteristic of the reference light LR and that of the measurement light LS.

The corner cube 70 changes the traveling direction of the reference light LR in the opposite direction. The corner cube 70 is movable in the direction along the incident optical path and the emitting optical path of the reference light LR. With this, the length of the optical path of the reference light LR is changed. It should be noted that it is sufficient to provide any one of a means for changing the length of the optical path of the measurement light LS and a means for changing the length of the optical path of the reference light LR.

The reference light LR that has passed through the corner cube 70 travels through the dispersion compensation member 69 and the optical path length correction member 68, is converted from the parallel light beam into a convergent light beam by the collimator 71, enters the optical fiber 72, is guided to the polarization controller 73. The polarization controller 73 regulates the polarization state of the reference light LR. Subsequently, the reference light LR is guided to the attenuator 75 by the optical fiber 74, and the light amount is adjusted under the control of the controller 100. The reference light LR whose light amount has been adjusted is guided to the fiber coupler 77 by the optical fiber 76.

Meanwhile, the measurement light LS generated by the fiber coupler 65 is guided by the optical fiber 51, is emitted from its fiber end face, and is made into a parallel light beam by the collimator lens 52. The measurement light LS that has been made into the parallel light beam is projected onto the subject's eye E via the optical scanner 41, the imaging lens 42, the deflection mirror 43, and the OCT objective lens 44. The measurement light LS is reflected and scattered at various depth positions of the subject's eye E. The returning light of the measurement light LS from the subject's eye E includes reflected light and backscattered light, advances in the same path as the forward path in the opposite direction, is led to the fiber coupler 65, and then reaches the fiber coupler 77 via the optical fiber 66B.

The fiber coupler 77 generates the interference light by superposing the measurement light LS incident via the optical fiber 66B and the reference light LR incident via the optical fiber 76 with each other (that is, by making the measurement light LS incident through the optical fiber 66B and the reference light LR incident through the optical fiber 76 interfere with each other). The fiber coupler 77 generates a pair of interference light beams LC by splitting the interference light generated from the measurement light LS and the reference light LR at a predetermined branching ratio (for example, 1:1). The pair of interference light beams LC emitted from the fiber coupler 77 are guided to the detector 79 by the optical fibers 78A and 78B, respectively.

The detector 79 is, for example, a balanced photo diode. The balanced photo diode includes a pair of photodetectors that respectively detect the pair of interference light beams LC, and outputs the difference between the detection results obtained by the pair of photodetectors. The detector 79 sends the difference result (detection signal) to the controller 100.

In the present embodiment, the illumination light and the measurement light LS are projected onto the subject's eye E in such a manner that the total light amount of the illumination light and the measurement light LS becomes equal to or less than a predetermined value. The total light amount is regulated by restricting the light amount of either the illumination light or the measurement light LS according to the operation mode designated in advance. The total light amount is the sum of the light amount of the illumination light and the light amount of the measurement light LS simultaneously projected onto the subject's eye E. The predetermined value is set in advance based on, for example, the value prescribed in a standard relating to protection of subject's eyes from light hazards. The OCT system 60 may include the light amount detector 80 that detects the light amount of the light L0 from the light source unit 61 or the light amount of the measurement light LS in order to monitor the total light amount described above. By detecting the light amount of the light L0 or that of the measurement light LS with the light amount detector 80, the controller 100 can specify the restriction amount of the light amount of the measurement light LS. Further, the controller 100 can specify the light amount of the illumination light, for example, by acquiring the control amount set for the light source of the illumination system 10. With this, while monitoring the light amount of the illumination light and that of the measurement light LS, the controller 100 can restrict the light amount of either the illumination light or the measurement light LS in such a manner that the total light amount becomes equal to or less than the predetermined value.

Although the swept source OCT is employed in the present example, it is also possible to employ other types of OCT such as the spectral domain OCT.

The controller 100 executes control of each part of the ophthalmological microscope system 1 (see FIG. 4). Examples of the control for the illumination system 10 include the followings: turning on of the light source, turning off of the light source, light amount adjustment of the light source, light amount detection of the light source; changing the aperture value of the diaphragm 10a; insertion and removal control of the ND filter 10b; and adjustment of the slit width in the case where slit illumination is possible. The light amount adjustment is the regulation of the light amount of the illumination light performed by setting the control amount for the light source. The light amount detection is the detection of the light amount of the illumination light performed by acquiring the control amount set for the light source. Examples of the control for the image sensor 23 include exposure adjustment, gain adjustment, photographing rate adjustment, and the like.

The controller 100 controls the display unit 31 to display various kinds of information. For example, the controller 100 controls the display unit 31L to display an image acquired by the image sensor 23L (or an image acquired by processing the image acquired by the image sensor 23L), and controls the display unit 31R to display an image acquired by the image sensor 23R (or an image acquired by processing the image acquired by the image sensor 23R).

As the control for the optical scanner 41, for example, the measurement light LS is deflected in a sequential manner so that the measurement light LS is projected to a plurality of positions according to an OCT scan pattern set in advance.

Parts of the OCT system 60 to be controlled include the light source unit 61, the attenuator 62a, the polarization controller 63, the corner cube 70, the polarization controller 73, the attenuator 75, the detector 79, and the light amount detector 80.

As described above, the attenuator 62a is provided between the light source unit 61 and the polarization controller 63, and adjusts the light amount of the light L0 from the light source unit 61. As the control for the attenuator 62a, the light amount of the light L0 is attenuated by the attenuation amount designated by the control signal.

The light amount detector 80 detects the light amount of the light L0 from the light source unit 61 or the light amount of the measurement light LS. For example, the optical path splitting member is disposed in the optical path of the light L0 or the optical path of the measurement light LS. By the optical path splitting member, a monitoring optical path branches from the optical path of the light L0 or from the optical path of the measurement light LS. The light amount detector 80 is disposed in the monitoring optical path ramified by the optical path splitting member. The light amount detector 80 includes, for example, a fiber coupler and a detector as in the configuration shown in FIG. 3. A detection signal generated by the light amount detector 80 is sent to the controller 100.

In addition, the controller 100 controls various mechanisms. As such mechanisms, the stereo angle changing unit 20A, the focusing unit 24A, the optical path deflector 25A, the interval changing unit 30A, and the orientation changing unit 30B are provided.

The stereo angle changing unit 20A relatively rotates the left light receiving system 20L and the right light receiving system 20R. That is, the stereo angle changing unit 20A relatively moves the left light receiving system 20L and the right light receiving system 20R so as to change the angle formed by the respective objective optical axes (for example, AL1 and AR1). This relative movement is performed, for example, in such a manner that the left light receiving system 20L and the right light receiving system 20R are moved by the same angle in the opposite rotation direction. In this movement mode, the direction of the bisector of the angle formed by the respective objective optical axes (for example, AL1 and AR1) is fixed. On the other hand, it is also possible to perform the aforementioned relative movement so that the direction of the bisector changes.

Figure 5:
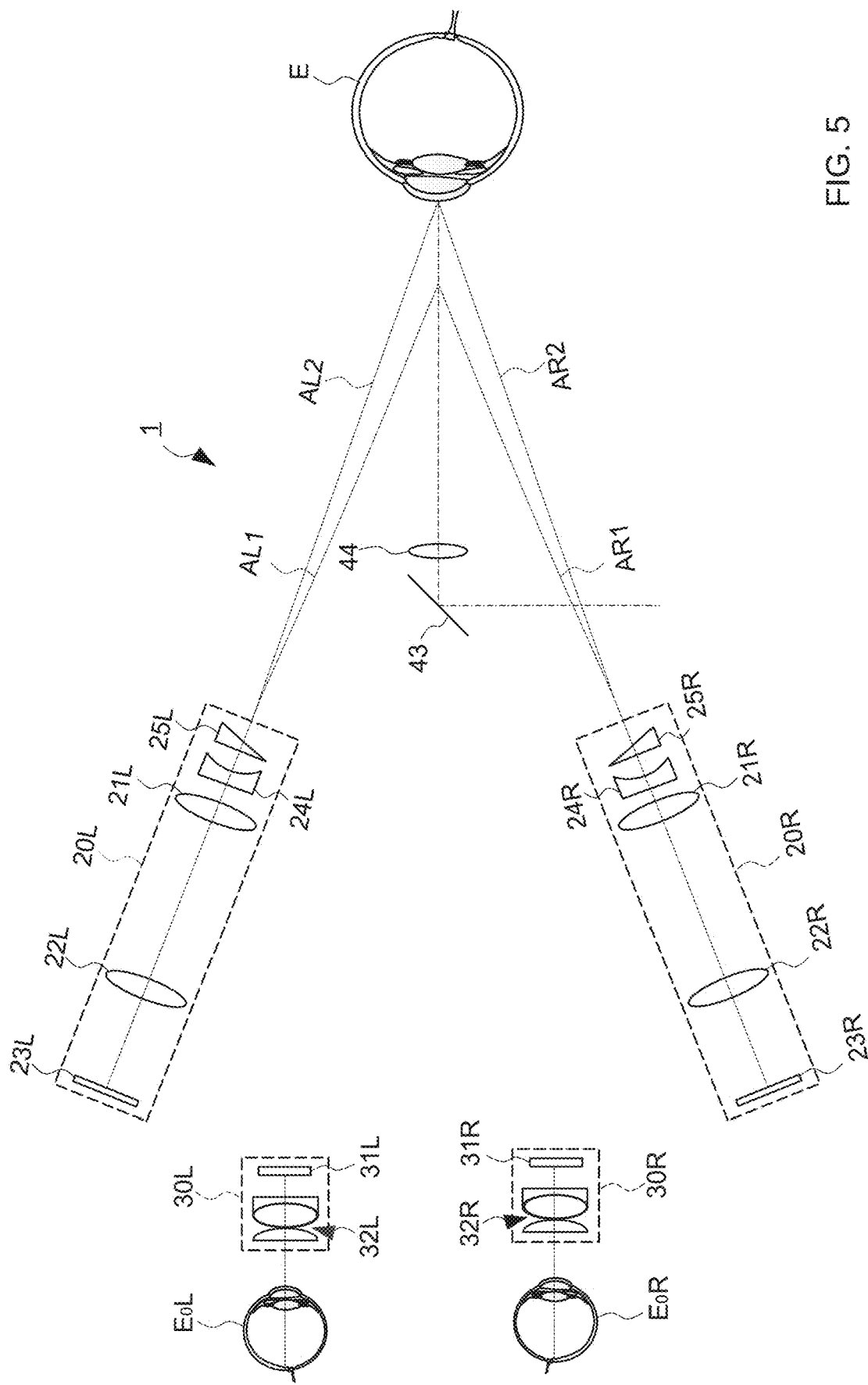
FIG. 5 is a schematic diagram illustrating an action of the ophthalmological microscope system according to the embodiment.

FIG. 5 shows an example of a state in which the stereo angle has been increased from the state shown in FIG. 2. Note that the stereo angle may be defined as an angle formed by the objective optical axis AL1 of the left light receiving system 20L and the objective optical axis AR1 of the right light receiving system 20R, or may be defined as an angle formed by the objective optical axis AL2 of the left light receiving system 20L and the objective optical axis AR2 of the right light receiving system 20R. Even if the stereo angle is changed by the stereo angle changing unit 20A, the relative positions (interval, relative orientation) of the left and right eyepiece systems 30L and 30R do not change. Also, it is possible to execute control so that the focal position does not move by adjusting the distance between the left and right light receiving systems 20L and 20R with respect to the subject's eye E and by changing the focal lengths of the left and right light receiving systems 20L and 20R in response to the change in the stereo angle.

The focusing unit 24A inserts and removes the left and right focus lenses 24L and 24R into and from the respective optical paths. The focusing unit 24A may be configured to simultaneously insert and remove the left and right focus lenses 24L and 24R. In another example, the focusing unit 24A may be configured to change the focal position by moving the left and right focus lenses 24L and 24R (simultaneously) in the respective directions along the optical axes. Alternatively, the focusing unit 24A may be configured to change the focal length by (simultaneously) changing the refractive powers of the left and right focus lenses 24L and 24R.

The optical path deflector 25A inserts and removes the left and right wedge prisms 25L and 25R into and from the respective optical paths. The optical path deflector 25A may be configured to simultaneously insert and remove the left and right wedge prisms 25L and 25R. In another example, the optical path deflector 25A may be configured to (simultaneously) change the prism amounts (and the prism directions) of the left and right wedge prisms 25L and 25R to change the respective directions along the optical paths of the left and right light receiving systems 20L and 20R.

The interval changing unit 30A changes the interval between the left and right eyepiece systems 30L and 30R. The interval changing unit 30A may be configured to relatively move the left and right eyepiece systems 30L and 30R without changing the relative orientation of their optical axes.

The orientation changing unit 30B changes the relative orientation of the left and right eyepiece systems 30L and 30R. The orientation changing unit 30B relatively moves the left eyepiece system 30L and the right eyepiece system 30R so as to change the angle formed by the respective optical axes. This relative movement is performed, for example, in such a manner that the left eyepiece system 30L and the right eyepiece system 30R are moved by the same angle in the opposite rotation direction. In this movement mode, the direction of the bisector of the angle formed by the respective optical axes is fixed. On the other hand, it is also possible to perform the aforementioned relative movement so that the direction of the bisector changes.

As described above, the controller 100 can specify the light amount of the illumination light and the light amount of the measurement light LS. Based on the light amount of the illumination light and the light amount of the measurement light LS specified, the controller 100 can execute the first light amount control to restrict the light amount of the measurement light LS in such a manner that the total light amount of the illumination light and the measurement light LS becomes equal to or less than the predetermined value. The controller 100 can restrict the light amount of the measurement light LS by controlling at least one of the light source unit 61 and the attenuator 62a. In addition, based on the light amount of the illumination light and the light amount of the measurement light LS specified, the controller 100 can execute the second light amount control to restrict the light amount of the illumination light in such a manner that the total light amount of the illumination light and the measurement light LS becomes equal to or less than the predetermined value. The controller 100 can restrict the light amount of the illumination light by controlling at least one of the light source of the illumination system 10, the projection angle of the illumination light onto the subject's eye E, the aperture value of the diaphragm 10a, and the ND filter 10b.

The controller 100 executes the first light amount control or the second light amount control according to the operation mode. In the present embodiment, the operation modes include an observation priority mode (or an illumination light priority mode) and an OCT priority mode (or an OCT light priority mode). The observation priority mode is an operation mode for simultaneously projecting the illumination light and the measurement light LS onto the subject's eye E while holding the light amount of the illumination light, by restricting the light amount of the measurement light LS in such a manner that the total light amount becomes equal to or less than the predetermined value. According to the observation priority mode, it is possible to improve the image quality of the observation image based on the returning light of the illumination light rather than the image quality of the OCT image, while securing the protection of the subject's eye from light hazards. The OCT priority mode is an operation mode for simultaneously projecting the illumination light and the measurement light LS onto the subject's eye E while holding the light amount of the measurement light LS, by restricting the light amount of the illumination light in such a manner that the total light amount becomes equal to or less than the predetermined value. According to the OCT priority mode, it is possible to improve the image quality of the OCT image rather than the image quality of the observation image, while securing the protection of the subject's eye from light hazards. Here, the controller 100 can execute at least one of the first light amount control and the second light amount control based on a detection result obtained by the light amount detector 80.

Note that the controller 100 may restrict the light amount of the measurement light LS or that of the illumination light by shortening the projection period of the measurement light LS or that of the illumination light onto the subject's eye E. As a result, it becomes possible to restrict the light amount of the measurement light LS or that of the illumination light without restricting the intensity of the measurement light LS or that of the illumination light. With this, the first light amount control or the second light amount control can be simplified.

Further, the controller 100 may control the detector 79 in such a manner that the sensitivity for detection of the interference light LC is increased in the observation priority mode. Examples of the control for the detector 79 include the increase in the gain applied to the detection signal obtained by the detector 79, the extension of the time for the acquisition of the detection signal, and the like. As a result, deterioration of the image quality of the OCT image can be suppressed even when the light amount of the measurement light LS is restricted in the observation priority mode.

The data processor 200 executes various kinds of data processing. Examples of such data processing include a process of forming an image, a process of manipulating (processing) an image, and the like. In addition, the data processor 200 may be capable of executing an analysis process of an image, an analysis process of an examination result, an analysis process of a measurement result, or a process relating to information on a subject (electronic medical record information etc.). The data processor 200 includes the zoom processor 210 and the OCT image forming unit 220.

The zoom processor 210 enlarges an image acquired by the image sensor 23. This processing is so-called digital zoom processing, and includes a process of clipping a part of the image acquired by the image sensor 23 and a process of generating an enlarged image of the part clipped. An area of the image to be clipped is set by the observer or by the controller 100. The zoom processor 210 applies the same processing to an image (left image) acquired by the image sensor 23L of the left light receiving system 20L and to the image (right image) acquired by the image sensor 23R of the right light receiving system 20R. With this, images of the same magnification are presented to the left eye $E_0L$ and the right eye $E_0R$ of the observer.

Note that it is possible to provide a so-called optical zoom function in addition to or in place of the digital zoom function described above. The optical zoom function is realized by providing a zoom lens (a zoom lens system) in each of the left and right light receiving systems 20L and 20R. As a specific example, the optical zoom function is realized by employing a configuration in which the zoom lenses can be (selectively) inserted into and removed from the respective optical paths, or a configuration in which the zoom lenses can be moved in the directions along the respective optical axes. Control relating to the optical zoom function is executed by the controller 100.

The OCT image forming unit 220 forms an image of the subject's eye E based on detection results of the interference light LC acquired by the detector 79 of the OCT system 60. The controller 100 sends the detection signals sequentially output from the detector 79 to the OCT image forming unit 220. The OCT image forming unit 220 forms a reflection intensity profile for each A line by applying Fourier transform and the like to the spectral distribution on the basis of the detection results acquired by the detector 79 for each series of wavelength scans (i.e., for each A line), for example. In addition, the OCT image forming unit 220 forms image data by applying an imaging process to each A line profile. With this, a B scan image (cross sectional image), volume data (three dimensional image data), and the like are obtained.

The data processor 200 may have a function of analyzing an image (OCT image) formed by the OCT image forming unit 220. Examples of such an analysis function include retinal thickness analysis, comparative analysis with normal eyes, and the like. Such an analysis function is executed using a known application. Further, the data processor 200 may have a function of analyzing an image acquired by the light receiving system 20. In addition, the data processor 200 may have an analysis function that combines the analysis of an image acquired by the light receiving system 20 and the analysis of an OCT image.

The user interface (UI) 300 has a function for exchanging information between an observer or the like and the ophthalmological microscope system 1. The user interface 300 includes a display device and an operation device (an input device). In the present embodiment, the user interface 300 is used, for example, for designating an operation mode of the ophthalmological microscope system 1, for instructing execution of the OCT measurement, and the like. The display device may include the display unit 31 and may include other display devices. The operation device includes various hardware keys and/or various software keys. It is possible to integrate at least part of the operation devices and at least part of the display devices. A touch panel display is one example of such an integrated configuration.

The communication unit 400 performs a process of sending information to other apparatuses and a process of receiving information sent from other apparatuses. The communication unit 400 may include a communication device conforming to a predetermined network (LAN, Internet, etc.). For example, the communication unit 400 acquires information from an electronic medical record database or a medical image database via a LAN provided in a medical institution. In the case where an external monitor is provided, the communication unit 400 can send an image (e.g., an image acquired by the light receiving system 20, an OCT image) acquired by the ophthalmological microscope system 1 to the external monitor substantially in real time.

The OCT system 60 is an example of the "interference optical system" according to the embodiment. The light source unit 61 is an example of the "OCT light source" according to the embodiment. The user interface 300 is an example of the "designation unit" according to the embodiment. The ND filter 10*b* is an example of the "filter" according to the embodiment.

Figure 6:
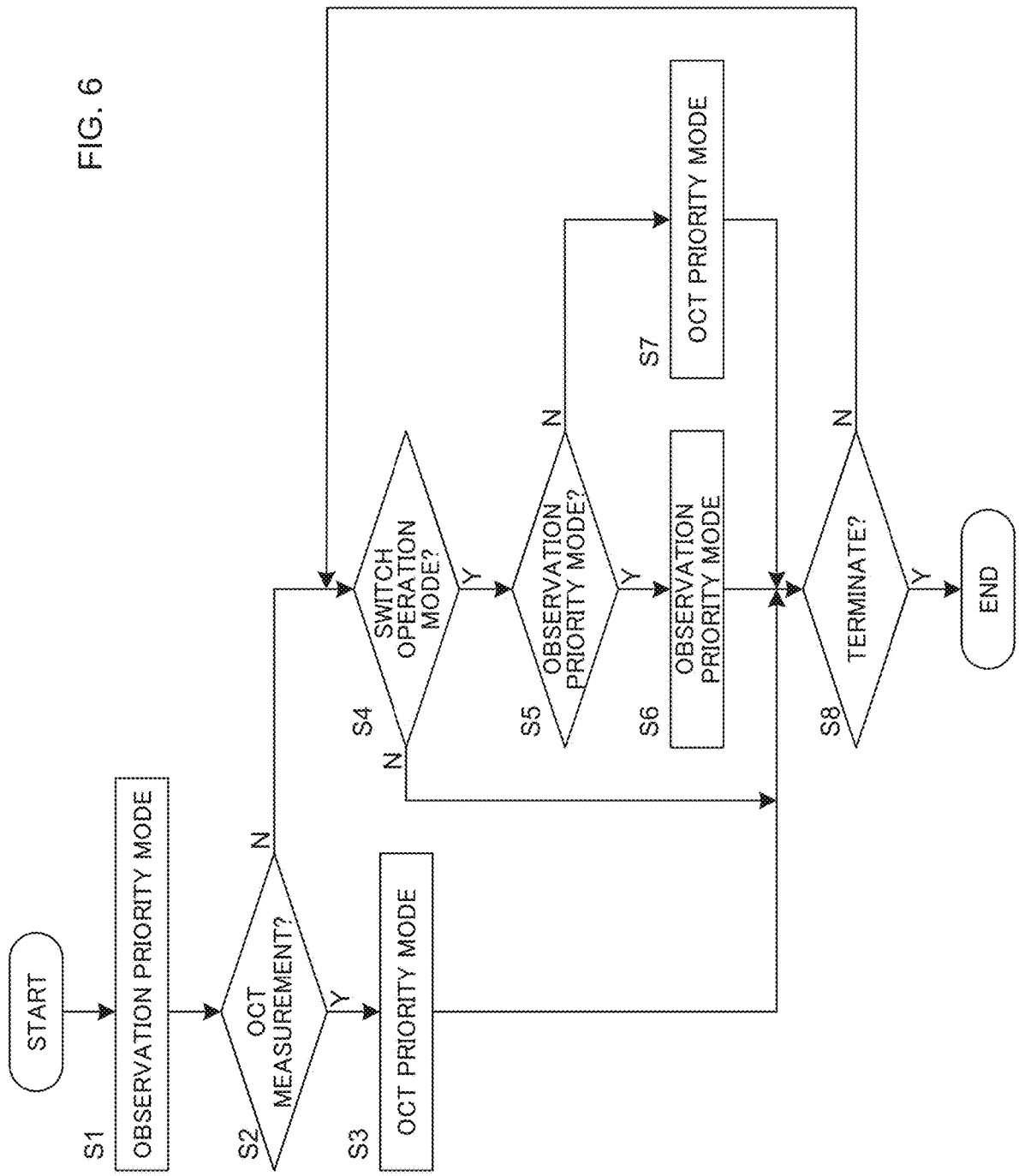
FIG. 6 is a flow chart illustrating an operation example of the ophthalmological microscope system according to the embodiment.

FIG. 6 shows a flow chart of an operation example of the ophthalmological microscope system 1 according to the embodiment. FIG. 6 presents an operation example in the case of switching the operation mode of the ophthalmological microscope system 1.

There are cases where the operation mode of the ophthalmological microscope system 1 is automatically designated by the controller 100 or manually designated by using the user interface 300. The controller 100 is capable of switching the operation mode of the ophthalmological microscope system 1 to the designated operation mode at an arbitrary timing.

When the power of the ophthalmological microscope system 1 is turned on, the controller 100 sets the operation mode of the ophthalmological microscope system 1 to the observation priority mode.

The controller 100 determines whether or not to execute the OCT measurement. For example, whether the OCT measurement is to be executed or not is instructed by the user using the user interface 300. The controller 100 can determine whether or not to execute the OCT measurement based on the content of operation performed on the user interface 300 by the user. When it has been determined to execute the OCT measurement (S2: Y), the operation of the ophthalmological microscope system 1 proceeds to S3.

When it has been determined not to execute the OCT measurement (S2: N), the operation of the ophthalmological microscope system 1 proceeds to S4.

When it has been determined to execute the OCT measurement (S2: Y), the controller 100 switches the operation mode of the ophthalmological microscope system 1 from the observation priority mode to the OCT priority mode. In the OCT priority mode, as described above, based on the light amount of the illumination light and the light amount of the measurement light LS specified, the light amount of the illumination light is restricted while holding the light amount of the measurement light LS so that the total light amount becomes equal to or less than the predetermined value. Then the operation of the ophthalmological microscope system 1 proceeds to S8.

When it has been determined not to execute the OCT measurement (S2: N), the controller 100 determines whether or not to switch the operation mode. For example, whether or not to switch the operation mode is instructed by the user using the user interface 300. The controller 100 can determine whether or not to switch the operation mode based on the content of the user's operation performed on the user interface 300. When it has been determined to switch the operation mode (S4: Y), the operation of the ophthalmological microscope system 1 proceeds to S5. When it has been determined not to switch the operation mode (S4: N), the operation of the ophthalmological microscope system 1 proceeds to S8.

When it has been determined to switch the operation mode (S4: Y), the controller 100 determines whether or not to switch to the observation priority mode. For example, the controller 100 can determine whether or not to switch to the observation priority mode based on the content of the user's operation performed on the user interface 300. When it has been determined to switch to the observation priority mode (S5: Y), the operation of the ophthalmological microscope system 1 moves to S6. When it has been determined not to switch to the observation priority mode (S5: N), the operation of the ophthalmological microscope system 1 proceeds to S7.

When it has been determined to switch to the observation priority mode (S5: Y), the controller 100 sets the observation priority mode as the operation mode after the switching. When the operation mode before the switching is the observation priority mode, the controller 100 does not change the operation mode (the observation priority mode continues). When the operation mode before the switching is the OCT priority mode, the controller 100 switches the operation mode from the OCT priority mode to the observation priority mode. In the observation priority mode, as described above, based on the light amount of the illumination light and the light amount of the measurement light LS specified, the light amount of the measurement light LS is restricted while holding the light amount of the illumination light so that the total light amount becomes equal to or less than the predetermined value. With this, even in the case of acquiring an OCT image during surgery, it is possible to acquire an observation image with high image quality while securing the protection of the subject's eye from light hazards. The operation of the ophthalmological microscope system 1 proceeds to S8.

When it has been determined not to switch to the observation priority mode (S5: N), the controller 100 sets the OCT priority mode as the operation mode after the switching. When the operation mode before the switching is the OCT priority mode, the controller 100 does not change the operation mode (the OCT priority mode continues). When the operation mode before the switching is the observation priority mode, the controller 100 switches the operation mode from the observation priority mode to the OCT priority mode. With this, even in the case of acquiring an OCT image during surgery, it is possible to temporarily acquire an OCT image with high image quality while securing the protection of the subject's eye from light hazards. Then, the operation of the ophthalmological microscope system 1 proceeds to S8.

The controller 100 determines whether or not to terminate the operation of the ophthalmological microscope system 1. For example, the termination of the operation is instructed by the user using the user interface 300. The controller 100 can determine whether or not to terminate the operation based on the content of the user's operation performed on the user interface 300. When it has been determined not to terminate the operation (S8: N), the operation of the ophthalmological microscope system 1 proceeds to S4. When it has been determined to terminate the operation (S8: Y), the ophthalmological microscope system 1 terminates the operation (end).

Effects of the ophthalmological microscope system of the embodiment will be described.

The ophthalmological microscope system according to the embodiment (the ophthalmological microscope system 1) includes an illumination system (the illumination system 10), a light receiving system (the light receiving system 20), an interference optical system (the OCT system 60), a designation unit (the user interface 300), and a controller (the controller 100). The illumination system is configured to project illumination light onto a subject's eye (the subject's eye E). The light receiving system is configured to guide returning light of the illumination light that has been projected onto the subject's eye to an image sensor (the image sensor 23) or an eyepiece system. The interference optical system is configured to split light (the light L0) from an OCT light source (the light source unit 61) into measurement light (the measurement light LS) and reference light (the reference light LR), and to detect interference light (the interference light LC) generated from the returning light of the measurement light projected onto the subject's eye and the reference light. The designation unit is used for designating an operation mode. The controller is configured to execute first light amount control that restricts the light amount of the measurement light in such a manner that the total light amount of the illumination light and the measurement light becomes equal to or less than a predetermined value when an observation priority mode has been designated using the designation unit. The controller is configured to execute second light amount control that restricts the light amount of the illumination light in such a manner that the total light amount becomes equal to or less than the predetermined value when an OCT priority mode has been designated using the designation unit.

According to such a configuration, the light amount of the illumination light or the measurement light is restricted in accordance with the operation mode in such a manner that the total light amount of the illumination light and the measurement light becomes a predetermined value. Therefore, it becomes possible to satisfy both the safety of the subject's eye and the improvement of the image quality according to the operation mode. With this, even when the interference optical system is combined with the light receiving system, it is possible to improve the image quality of the image corresponding to the operation mode while securing the protection of the subject's eye from light hazards.

Further, the ophthalmological microscope system according to the embodiment may include a light amount detector (the light amount detector 80). The light amount detector is configured to detect the light amount of the light from the OCT light source or the measurement light. The controller executes at least one of the first light amount control and the second light amount control based on a detection result obtained by the light amount detector.

According to such a configuration, based on the detection result of the light amount of the light from the OCT light source or the measurement light, it is possible to restrict the light amount of either the illumination light or the measurement light LS in such a manner that the total light amount becomes equal to or less than the predetermined value.

Further, the ophthalmological microscope system according to the embodiment may include an attenuator (the attenuator 62*a*). The attenuator is configured for regulating the light amount of the light from the OCT light source or the measurement light. The controller controls at least one of the OCT light source and the attenuator to restrict the light amount of the measurement light.

According to such a configuration, it is possible to restrict the light amount of the measurement light easily and with high precision in the observation priority mode.

Further, in the ophthalmological microscope system according to the embodiment, the illumination system may be capable of changing the projection angle of the illumination light onto the subject's eye. The illumination system includes a diaphragm (the diaphragm 10*a*) and a filter (the ND filter 10*b*). The aperture value of the diaphragm is variable. The filter can be inserted into and removed from the optical path of the illumination light. The controller controls at least one of a light source of the illumination system, the projection angle, the aperture value and the filter to restrict the light amount of the illumination light.

According to such a configuration, it is possible to restrict the light amount of the illumination light easily and with high precision in the OCT priority mode.

Further, in the ophthalmological microscope system according to the embodiment, the controller may shorten the projection period of the measurement light or the illumination light onto the subject's eye to restrict the light amount of the measurement light or the illumination light.

According to such a configuration, it is possible to restrict the light amount of the measurement light or the illumination light without restricting the intensity of the measurement light or the illumination light, and it is possible to simplify the first light amount control or the second light amount control.

Further, in the ophthalmological microscope system according to the embodiment, the interference optical system may include a detector (the detector 79). The detector is configured to detect the interference light. The controller controls the detector in such a manner that the sensitivity for detection of the interference light increases when the observation priority mode has been designated.

According to such a configuration, deterioration of the image quality of the image formed based on the detection result of the interference light can be reduced even when the light amount of the measurement light is restricted in the observation priority mode.

The above embodiment is merely an example for implementing the present invention. Those who intend to implement the present invention may apply any modification, omission, addition, substitution, etc. within the scope of the gist of the present invention. Hereinafter, the drawings in the above embodiment will be referred to as needed.

In the above-described embodiment, the focus lenses 24L and 24R and the wedge prisms 25L and 25R are removed from the respective optical paths at the time of observing the eye fundus and are inserted into the respective optical paths at the time of observing the anterior eye segment. Such an operation can be automated. In an embodiment, a supplementary optical member for changing the observation site of the subject's eye is used. For example, the front lens 90 is disposed in the optical path at the time of observing the eye fundus, and is removed from the optical path at the time of observing the anterior eye segment.

The ophthalmological microscope system of the present modification example changes the states of the focus lenses 24L and 24R according to the state of the supplementary optical member (that is, according to the selection of the observation site). In other words, the controller 100 controls a second mechanism for interlockingly operating the focus lenses 24L and 24R according to the change of the observation site by means of the supplementary optical member. Similarly, the controller 100 controls a third mechanism for interlockingly operating the wedge prisms 25L and 25R according to the change of the observation site by means of the supplementary optical member.

A specific example will be described. In response to the removal of the front lens 90 from the optical path, the controller 100 controls the focusing unit 24A and the optical path deflector 25A so as to insert the focus lenses 24L and 24R and the wedge prisms 25L and 25R into the respective optical paths. Conversely, in response to the insertion of the front lens 90 into the optical path, the controller 100 controls the focusing unit 24A and the optical path deflector 25A so as to remove the focus lenses 24L and 24R and the wedge prisms 25L and 25R from the respective optical paths.

The ophthalmological microscope system of the present modification example may have a configuration for generating information indicating the state of the supplementary optical member (for example, whether or not the front lens 90 is inserted into the optical path). For example, the disposition state of an arm that holds the front lens 90 can be detected by using a sensor such as a micro switch. Alternatively, when the insertion and removal of the front lens 90 is performed based on a signal from the controller 100, the current state of the front lens 90 can be recognized by referring to the history of control.

As another example, based on the image(s) acquired by the image sensors 23L and/or 23R and the current states of the focus lenses 24L and 24R and the wedge prisms 25L and 25R, it is possible to determine whether or not the front lens 90 is disposed in the optical path. For example, by analyzing the image acquired in the state where the focus lens 24L and the like are disposed in the optical path, the data processor 200 calculates the amount indicating the blur state of the image acquired. When the blur amount is equal to or more than a threshold value, it is determined that the front lens 90 is disposed in the optical path. Conversely, when the blur amount is less than the threshold value, it is determined that the front lens 90 is removed from the optical path. It is possible to determine the state of the front lens 90 in a similar manner also in the case of analyzing the image acquired in the state where the focus lens 24L and the like are removed from the optical path.

According to the present modification example, the states of the lenses (the focus lenses 24L and 24R) for changing the focal positions and the states of the deflecting members (the wedge prisms 25L and 25R) for deflecting the optical paths can be automatically changed in response to the switching of the observation sites. With this, it becomes possible to further improve the operability.

Figure 7:
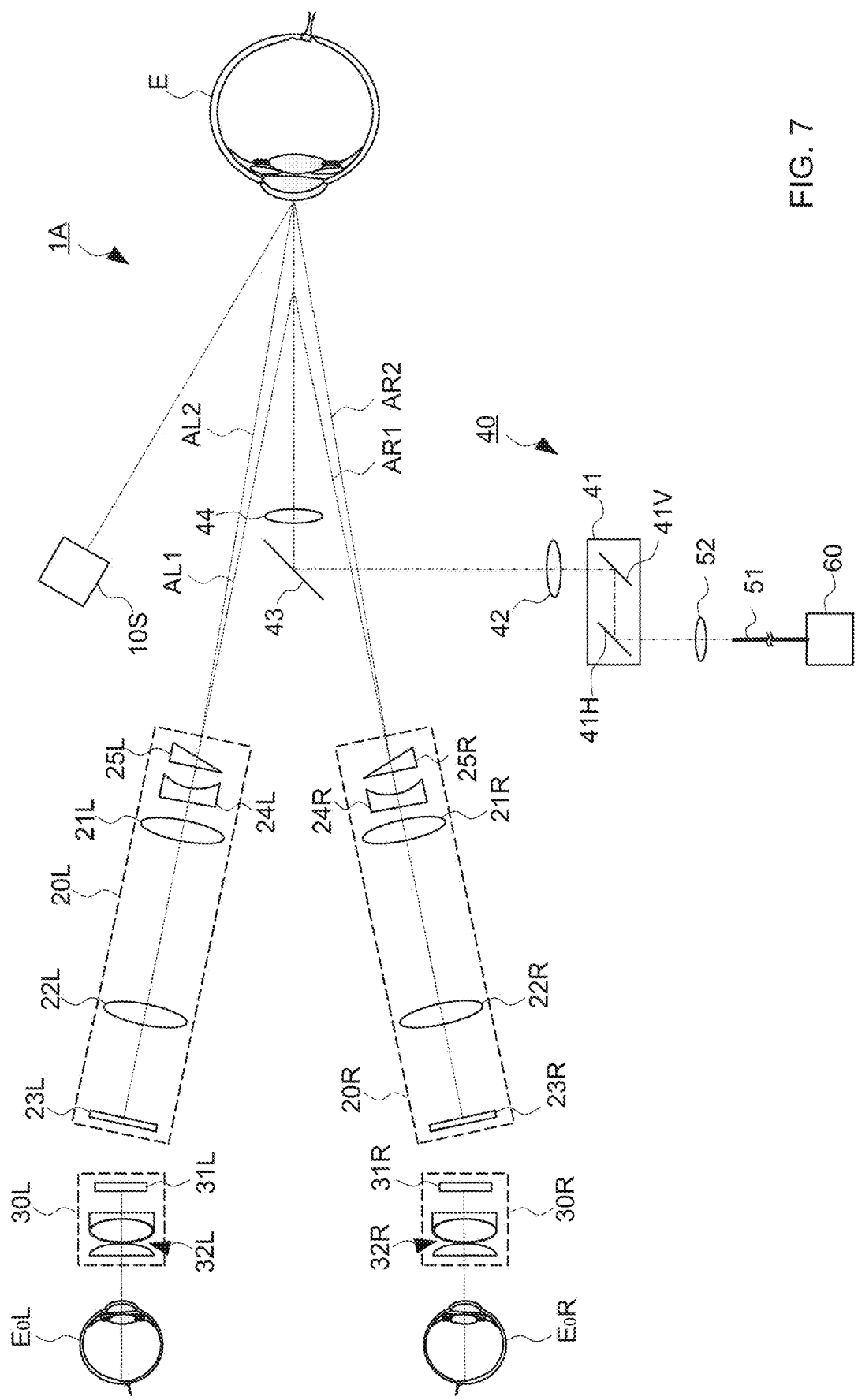
FIG. 7 is a schematic diagram illustrating an example of the configuration of the ophthalmological microscope system according to the modification example.

The illumination systems (10L and 10R) of the above embodiment are disposed coaxially with the pair of light receiving systems (20L and 20R). The present modification example will describe a configuration in which the illumination systems are disposed non-coaxially with the pair of light receiving systems, that is, a configuration capable of projecting the illumination light from a direction different from the objective optical axes of the pair of light receiving systems. An example of the configuration of the optical system according to the present modification example is shown in FIG. 7. The illumination system 10S of the ophthalmological microscope system 1A is an additional illumination system and can, for example, project slit light onto the subject's eye. A typical example of such an ophthalmological microscope is a slit lamp microscope. In the present modification example, like the slit lamp microscope, the relative position between the illumination system 10S and the light receiving systems 20L and 20R can be changed. In other words, the illumination system 10S and the light receiving systems 20L and 20R are configured to be rotatable about the same axis. As a result, it becomes possible to observe a cross section of the cornea etc. that is being illuminated with the slit light from an oblique direction.

The slit light emitted from the illumination system 10S corresponds to part or all of the illumination light according to the above embodiment. In other words, the slit light emitted from the illumination system 10S and the illumination light according to the above embodiment can be applied to the above embodiment as the illumination light according to the present modification example. In this case, the controller of the ophthalmological microscope system 1A can execute the first light amount control that restricts the light amount of the measurement light LS in such a manner that the total light amount of the slit light emitted from the illumination system 10S, the illumination light and the measurement light LS becomes equal to or less than the predetermined value. In addition, the controller can execute the second light amount control that restricts the light amount of the slit light or the illumination light in such a manner that the total light amount of the slit light emitted from the illumination system 10S, the illumination light and the measurement light LS becomes equal to or less than the predetermined value. The controller can restrict the light amount of the slit light by controlling a light source of the illumination system 10S, a diaphragm or a filter etc. included in the illumination system 10S, or the like.

An ophthalmological microscope system may include one or both of a coaxial illumination system as in the embodiment described above and a non-coaxial illumination system as in the present modification example. In the case of including both illumination systems, it is possible to switch the illumination system to be used, for example, in accordance with the switching of the observation sites.

In the above embodiment or modification examples, the case has been described in which the light amount of the illumination light or the measurement light is restricted so that the total light amount of the illumination light and the measurement light becomes equal to or less than the predetermined value. On the other hand, the light amount of the illumination light or the measurement light may be restricted so that the total light amount of the illumination light and the measurement light becomes less than a predetermined value.

In the above embodiment or modification examples, the restriction of the light amount of the measurement light in the first light amount control may include making the light amount of the measurement light zero (i.e., stopping the projection of the measurement light). Also, the restriction of the light amount of the illumination light in the second light amount control may include making the light amount of the illumination light substantially zero (i.e., the light amount of the illumination light>0).

In the above embodiment or modification examples, the ND filter has been described as an example of a filter that can be inserted into and removed from the optical path of the illumination light. However, the filter that can be inserted into and removed from the optical path of the illumination light may be a filter other than the ND filter.

The invention claimed is:

1. An ophthalmological microscope system comprising:
an illumination system configured to project illumination light onto a subject's eye;
a light receiving system configured to guide returning light of the illumination light that has been projected onto the subject's eye to an image sensor or an eyepiece system;
an interference optical system configured to split light from an OCT light source into measurement light and reference light and detect interference light generated from returning light of the measurement light projected onto the subject's eye and the reference light;
a designation unit used for designating an operation mode; and
a controller configured to execute first light amount control that restricts light amount of the measurement light to make total light amount of the illumination light and the measurement light equal to or less than a predetermined value when an observation priority mode has been designated using the designation unit, and execute second light amount control that restricts light amount of the illumination light to make the total light amount equal to or less than the predetermined value when an OCT priority mode has been designated using the designation unit.

2. The ophthalmological microscope system of claim 1, further comprising a light amount detector configured to detect light amount of the light from the OCT light source or the measurement light, wherein the controller executes at least one of the first light amount control and the second light amount control based on a detection result obtained by the light amount detector.

3. The ophthalmological microscope system of claim 1, further comprising an attenuator configured for adjusting light amount of the light from the OCT light source or the measurement light,
wherein the controller controls at least one of the OCT light source and the attenuator to restrict the light amount of the measurement light.

4. The ophthalmological microscope system of claim 1, wherein
the illumination system is capable of changing projection angle of the illumination light onto the subject's eye,
the illumination system comprises:
a diaphragm whose aperture value is variable; and
a filter that can be inserted into and removed from an optical path of the illumination light, and
the controller controls at least one of a light source in the illumination system, the projection angle, the aperture value and the filter to restrict the light amount of the illumination light.

5. The ophthalmological microscope system of claim 1, wherein the controller shortens a projection period of the measurement light or the illumination light onto the subject's eye to restrict the light amount of the measurement light or the illumination light.

6. The ophthalmological microscope system of claim 1, wherein
the interference optical system comprises a detector configured to detect the interference light, and
the controller controls the detector to increase sensitivity for detection of the interference light when the observation priority mode has been designated.

7. The ophthalmological microscope system of claim 2, further comprising an attenuator configured for adjusting light amount of the light from the OCT light source or the measurement light,
wherein the controller controls at least one of the OCT light source and the attenuator to restrict the light amount of the measurement light.

8. The ophthalmological microscope system of claim 2, wherein
the illumination system is capable of changing projection angle of the illumination light onto the subject's eye,
the illumination system comprises:
a diaphragm whose aperture value is variable; and
a filter that can be inserted into and removed from an optical path of the illumination light, and
the controller controls at least one of a light source in the illumination system, the projection angle, the aperture value and the filter to restrict the light amount of the illumination light.

9. The ophthalmological microscope system of claim 3, wherein
the illumination system is capable of changing projection angle of the illumination light onto the subject's eye,
the illumination system comprises:
a diaphragm whose aperture value is variable; and
a filter that can be inserted into and removed from an optical path of the illumination light, and
the controller controls at least one of a light source in the illumination system, the projection angle, the aperture value and the filter to restrict the light amount of the illumination light.

10. The ophthalmological microscope system of claim 2, wherein the controller shortens a projection period of the measurement light or the illumination light onto the subject's eye to restrict the light amount of the measurement light or the illumination light.

11. The ophthalmological microscope system of claim 3, wherein the controller shortens a projection period of the measurement light or the illumination light onto the subject's eye to restrict the light amount of the measurement light or the illumination light.

12. The ophthalmological microscope system of claim 4, wherein the controller shortens a projection period of the measurement light or the illumination light onto the subject's eye to restrict the light amount of the measurement light or the illumination light.

13. The ophthalmological microscope system of claim 2, wherein
the interference optical system comprises a detector configured to detect the interference light, and
the controller controls the detector to increase sensitivity for detection of the interference light when the observation priority mode has been designated.

14. The ophthalmological microscope system of claim 3, wherein
the interference optical system comprises a detector configured to detect the interference light, and the controller controls the detector to increase sensitivity for detection of the interference light when the observation priority mode has been designated.

15. The ophthalmological microscope system of claim 4, wherein the interference optical system comprises a detector configured to detect the interference light, and the controller controls the detector to increase sensitivity for detection of the interference light when the observation priority mode has been designated.

16. The ophthalmological microscope system of claim 5, wherein the interference optical system comprises a detector configured to detect the interference light, and the controller controls the detector to increase sensitivity for detection of the interference light when the observation priority mode has been designated.

* * * * *